US010450525B2

(12) United States Patent
Suen et al.

(10) Patent No.: US 10,450,525 B2
(45) Date of Patent: Oct. 22, 2019

(54) PROCESS FOR ALAKNOLAMIDE SYNTHESIS

(71) Applicant: Chevron Oronite Company LLC, San Ramon, CA (US)

(72) Inventors: Yat Fan Suen, Martinez, CA (US); Joanne Liu, Richmond, CA (US); Francois Simard, Novato, CA (US); Yuen Ting Anita Leung, San Pablo, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 1022 days.

(21) Appl. No.: 14/469,924

(22) Filed: Aug. 27, 2014

(65) Prior Publication Data

US 2016/0060560 A1  Mar. 3, 2016

(51) Int. Cl.
*C07C 231/02* (2006.01)
*C10L 10/08* (2006.01)
*C07C 231/22* (2006.01)
*C10M 105/62* (2006.01)

(52) U.S. Cl.
CPC ............ *C10L 10/08* (2013.01); *C07C 231/02* (2013.01); *C07C 231/22* (2013.01); *C10M 105/62* (2013.01); *C10L 2200/04* (2013.01)

(58) Field of Classification Search
CPC ....... C10M 2207/281; C10M 2207/282; C10L 1/2222
USPC .................................. 508/463, 496; 44/405
See application file for complete search history.

(56) References Cited

U.S. PATENT DOCUMENTS

| 3,036,003 | A | 5/1962 | Verdol |
| 3,172,892 | A | 3/1965 | Le Suer |
| 3,219,666 | A | 11/1965 | Norman |
| 3,272,746 | A | 9/1966 | Suer et al. |
| 3,275,554 | A | 9/1966 | Wagenaar |
| 3,329,658 | A | 7/1967 | Fields |
| 3,438,757 | A | 4/1969 | Anderson et al. |
| 3,449,250 | A | 6/1969 | Fields |
| 3,454,555 | A | 7/1969 | Jong et al. |
| 3,565,804 | A | 2/1971 | Anderson et al. |
| 3,586,629 | A | 6/1971 | Frank et al. |
| 3,591,598 | A | 7/1971 | Little et al. |
| 3,666,730 | A | 5/1972 | Coleman |
| 3,980,569 | A | 9/1976 | Pindar et al. |
| 4,085,126 | A | 4/1978 | McConnell et al. |
| 4,234,435 | A | 11/1980 | Meinhardt et al. |
| 4,612,132 | A | 9/1986 | Wollenberg et al. |
| 4,729,769 | A | 3/1988 | Schlicht et al. |
| 4,746,446 | A | 5/1988 | Wollenberg et al. |
| 5,716,912 | A | 2/1998 | Harrison et al. |
| 6,165,235 | A | 12/2000 | Kolp et al. |

(Continued)

FOREIGN PATENT DOCUMENTS

JP  08198830  8/1996
WO  2009050256  4/2009

Primary Examiner — Vishal V Vasisth
(74) Attorney, Agent, or Firm — Ryan, Mason & Lewis, LLP

(57) ABSTRACT

The present invention is directed to a process of making alkanolamides wherein the "aging" time is reduced and the diethanol amide to ester ratio in the finished product is increased. Further provided is an additive composition comprising an alkanolamide which contains a reduced amount of DEA and BHEP.

27 Claims, 2 Drawing Sheets

(56) References Cited

U.S. PATENT DOCUMENTS

| | | |
|---|---|---|
| 6,372,696 B1 | 4/2002 | Tipton |
| 6,440,905 B1 | 8/2002 | Epps et al. |
| 6,559,194 B2 * | 5/2003 | Malwitz .................. C08K 5/103 521/142 |
| 2005/0049550 A1 | 3/2005 | Kirchhofer et al. |
| 2005/0097813 A1 | 5/2005 | Lambert et al. |
| 2005/0107623 A1 | 5/2005 | Fox et al. |
| 2007/0123437 A1 | 5/2007 | Boffa et al. |
| 2007/0142237 A1 * | 6/2007 | DeGonia .............. C10M 141/12 508/187 |
| 2008/0072477 A1 | 3/2008 | Colucci et al. |
| 2010/0132253 A1 | 6/2010 | Kaufman et al. |

\* cited by examiner

PROCESS FOR ALAKNOLAMIDE SYNTHESIS

FIELD OF THE INVENTION

The present invention generally relates to an improved process for alkanolamide synthesis.

BACKGROUND OF THE INVENTION

Liquid hydrocarbon fuel burning engines are used in a wide variety of applications including automotive, transportation, marine, electricity generation and compressors. Such engines are often relatively inefficient and may emit significant quantities of pollutant gases and particles. This is of particular concern when the engines are used in built up areas, e.g. cities where the resultant pollution affects significant numbers of people, but is also of significant concern in other situations.

Liquid hydrocarbon fuels typically include a number of additives to improve the efficiency of combustion, reduce pollutant levels, modify combustion characteristics of the fuel and maintain engine cleanliness (i.e., through use of dispersants and detergents).

Additives which can reduce friction levels or otherwise improve efficiency in an engine are of particular interest as they can improve fuel economy. It is sufficient to say that even a small improvement in fuel economy would have massive impact on a global scale.

Alkanolamide based friction modifiers are one family of chemicals which have been identified to provide significant utility as a fuel additive or as a lubricating oil additive. Alkanolamides are formed by the reaction of fatty acids and/or their esters with diethanolamine (DEA). However, there is a significant problem with existing methods of manufacture of alkanolamides and the by-products formed thereby. It has been found that by-products are prone to form throughout the reaction process. A particularly troublesome impurity formed in the course of this reaction is bis-hydroxyethyl piperazine (BHEP). This has significant implications in that, when the composition is used as a fuel additive, BHEP may block fuel inlets or cause other undesirable build ups in the engine.

Additionally, problems exist in the manufacture of alkanolamides in that significant levels of unreacted fatty acids and/or esters and DEA remain in the final product. It has been well documented that amines can wreak havoc on fluorocarbon based elastomer seals. In this regard, if the amount of unreacted DEA could be reduced, a benefit in engine efficiency could be realized.

The reaction scheme below is a typical synthetic procedure for making diethanol amide.

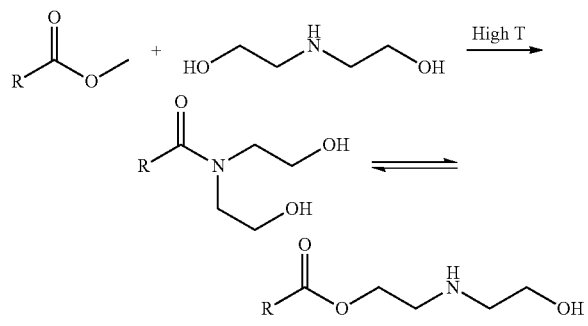

The procedure involves reacting fatty acid methyl ester with diethanol amine under high temperatures, i.e. 150° C. The drawback of the procedure is that the product is equilibrium between the diethanol amide and ester amine. Prolonged reaction will not drive the reaction to a state where most of the product is diethanol amide which is the desired product. Rather, the equilibrium state stays relatively unchanged at an unfavorable level. Ester amine causes harm issues and is unstable and labile for hydrolysis and formation of non-active species. On the other hand, in the product, there is about 4-7% diethanol amine left over in the product. This is capable of causing corrosion and other harm issues.

Production by industrial scale has proven that even after prolonged reaction time, i.e. 5 hours, the diethanol amide and ester amine ratio is still unsatisfactory. This is reflected by a low amide to ester IR ratio of approximately 2. It typically takes another 3 months "aging" at room temperature for the product to equilibrate to an amide to ester ratio of 3.8 while reducing the DEA content to about 1.5% level.

Herein, we report a process which can quickly shorten the "aging" process for diethanol amide synthesis from several months to a few days. The diethanol amide product has reduced residual diethanol amine content, and the product has the added benefit of less harm issues.

In general, the following patent art teaches elements of the proposed invention, but none are capable of producing an alkanolamide which contains a reduced amount of DEA and BHEP, and in which the diethanol amide to ester ratio in the finished product is increased.

US patent application number US 20080072477 discloses an alkanolamide composition as fuel additive for gasoline grade fuel and liquid hydrocarbon fuel and friction modifying additive which contains a fatty acid and diethanolamine, which contains a specified concentration of bis-hydroxyethyl piperazine. Controlling the rate of addition of diethanolamine and other reaction parameters contribute to a reduction in formation of bis-hydroxyethyl piperazine.

U.S. Pat. No. 4,085,126 discloses fatty alkanol-amide detergent compositions prepared by alkoxylation of a fatty acid followed by transesterification with alkanolamine.

WO 2009050256 discloses a fuel additive for additive package obtained by reacting carboxylic acid compound with alkanol amine under reaction conditions supporting formation of fuel additive containing polysubstituted alkanol amine derivative.

US patent application number US 20050107623 discloses production of hydroxyalkyl amide as friction modifiers for fuel in automotive industry involves reacting primary and secondary alkanolamine with ester optionally in presence of catalyst and in presence of metal silicate.

US 20050097813 teaches a method of purification of hydroxyalkyl amide composition from alkanolamine and ester and/or fatty natural material involves adding non-polar solvent; heating to extraction temperature; adding aqueous salt solution; and separating organic phase.

U.S. Pat. No. 4,729,769 discloses a motor fuel composition containing a detergent additive reaction product of a fatty acid ester and a hydroxy hydrocarbyl amine. JP 08198830 teaches fatty acid diethanolamide-type surfactant preparation with low diethanolamine content by reacting diethanolamine with a fatty acid or its ester or glyceride and subjecting to reverse osmosis.

US patent application number US 20100132253 teaches a fuel additive useful for providing friction modification in internal combustion engine with a friction modifying amount of alkanolamide, where the additive is free of esters or specific molar ratio of amides to esters within additive.

It is therefore desirable for a process of making alkanolamides wherein the "aging" time is reduced and the diethanol amide to ester ratio in the finished product is increased. Further, it is desirable to provide an additive composition comprising an alkanolamide which contains a reduced amount of DEA and BHEP, and which is suitable for use as a liquid hydrocarbon fuel additive or a lubricating oil additive.

SUMMARY OF THE INVENTION

In accordance with one embodiment of the present invention, there is provided a method for aging a composition comprising the steps of:
a) providing a mixture comprising:
   i. an amide reaction product of a fatty alkyl ester and alkanolamine,
   ii. an ester reaction product of the fatty alkyl ester and the alkanolamine, and
b) maintaining the mixture from (a) at a temperature from 70° C. to 90° C. for a period of time sufficient to increase the ratio of the amide reaction product to the ester reaction product by at least 5%.

Also provided is a method for aging a composition comprising the steps of:
a) providing a reaction mixture comprising a fatty acid alkyl ester, an alkanolamine, and a reaction product of a fatty acid alkyl ester and an alkanolamine, wherein the reaction product comprises:
   i. an amide reaction product,
   ii. an ester reaction product, and
b) maintaining the mixture from (a) at a temperature from 70° C. to 90° C. for a period of time sufficient to increase the ratio of the amide reaction product to the ester reaction product by at least 5%.

Definitions

The following terms will be used throughout the specification and will have the following meanings unless otherwise indicated.

The term "a major amount" of a base oil refers to where the amount of the base oil is at least 40 wt. % of the lubricating oil composition. In some embodiments, "a major amount" of a base oil refers to an amount of the base oil more than 50 wt. %, more than 60 wt. %, more than 70 wt. %, more than 80 wt. %, or more than 90 wt. % of the lubricating oil composition.

The term BHEP refers to "bis-hydroxyethyl piperazine".

The term DEA refers to "diethanolamine".

The term A/E ratio (Amide to Ester ratio) refers to the ratio of alkanolamide to ester in the finished product.

In the following description, all numbers disclosed herein are approximate values, regardless whether the word "about" or "approximate" is used in connection therewith. They may vary by 1 percent, 2 percent, 5 percent, or, sometimes, 10 to 20 percent.

DETAILED DESCRIPTION OF THE INVENTION

Figure 1:
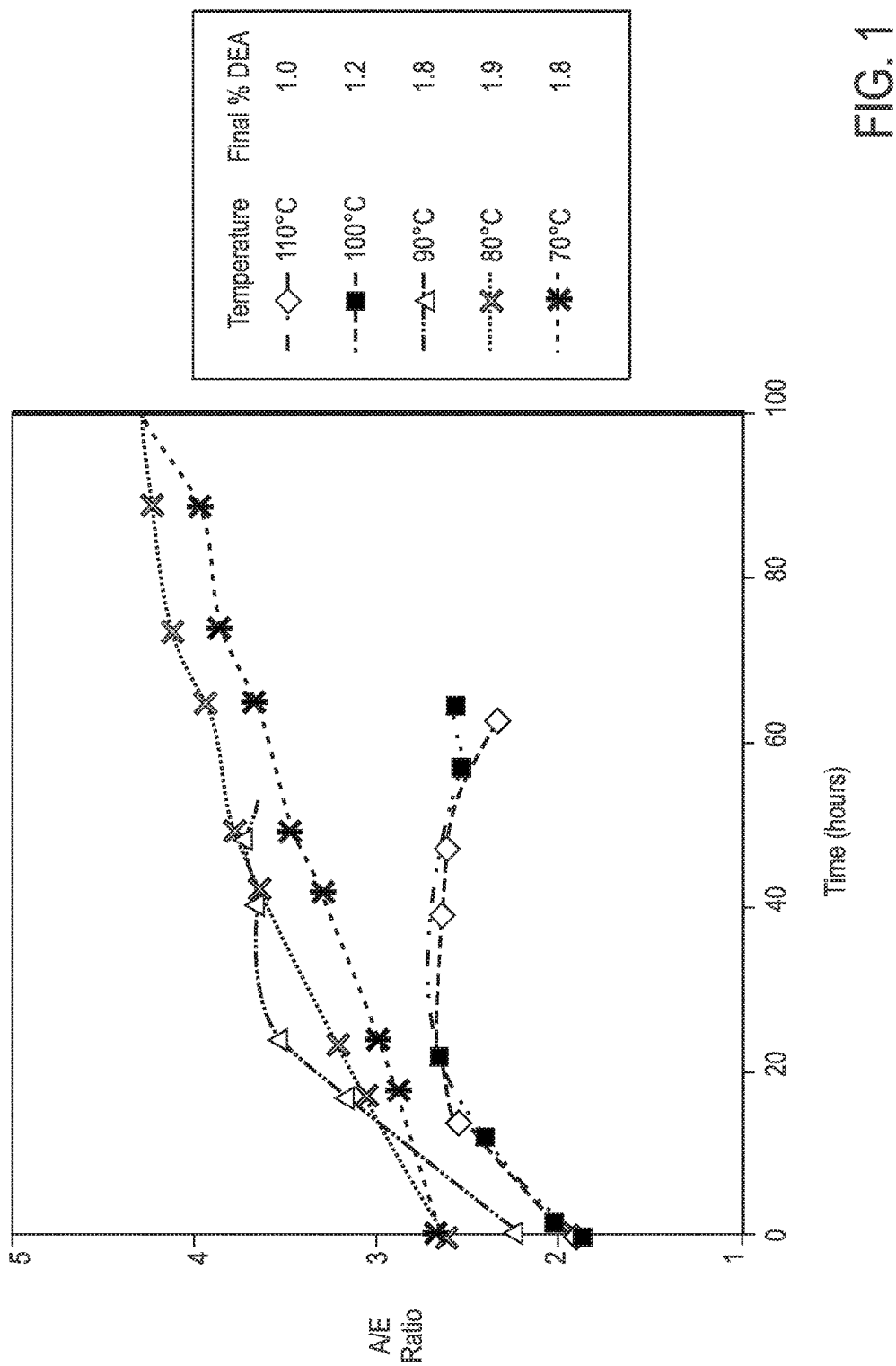
FIG. 1 shows the aging of Example 2 at 70° C., 80° C., 90° C., 100° C., and 110° C. and the effect these various temperatures have on the amide/ester ratio at various time intervals.

In general, provided herein is a method for aging a composition comprising the steps of:
a) providing a mixture comprising:
   i. an amide reaction product of a fatty alkyl ester and alkanolamine,
   ii. an ester reaction product of the fatty alkyl ester and the alkanolamine, and
b) maintaining the mixture from (a) at a temperature from 70° C. to 90° C. for a period of time sufficient to increase the ratio of the amide reaction product to the ester reaction product by at least 5%.

Also provided is a method for aging a composition comprising the steps of:
a) providing a reaction mixture comprising a fatty acid alkyl ester, an alkanolamine, and a reaction product of a fatty acid alkyl ester and an alkanolamine, wherein the reaction product comprises:
   i. an amide reaction product,
   ii. an ester reaction product, and
b) maintaining the mixture from (a) at a temperature from 70° C. to 90° C. for a period of time sufficient to increase the ratio of the amide reaction product to the ester reaction product by at least 5%.

In one embodiment the fatty acid ester is a $C_4$ to about $C_{75}$, preferably about $C_6$ to about $C_{24}$, preferably about $C_6$ to about $C_{20}$, preferably about $C_6$ to about $C_{18}$, preferably about $C_8$ to about $C_{18}$, preferably $C_8$ to $C_{16}$, preferably $C_8$ to $C_{12}$ fatty acid ester. These fatty acid esters may be characterized by the formula RCOOH wherein R is an alkyl hydrocarbon group containing from about 7 to about 15, preferably from about 11 to about 13, and preferably about 11 carbon atoms. The term "alkyl" refers to a $C_3$ to $C_{74}$ saturated aliphatic groups including straight-chain, branched-chain and cyclic groups. The alkyl group can have varying degrees of unsaturation (i.e., alkenes and alkynes present). The alkyl group can be substituted with substituents.

In general, a $C_4$ to about $C_{75}$ fatty acid monoalcohol ester is a reaction product of one or more fatty acids with one or more monoalcohols. The fatty acid monoalcohol esters can contain from about $C_4$ to about $C_{75}$ fatty acid monoalcohol esters or from about $C_6$ to about $C_{24}$ fatty acid monoalcohol esters or from about $C_8$ to about $C_{22}$ fatty acid monoalcohol esters. As one skilled in the art will readily appreciate, the about $C_4$ to about $C_{75}$ fatty acid monoalcohol esters can be the same or different fatty acid monoalcohol esters. Fatty acids are a class of compounds containing a long hydrocarbon chain and a terminal carboxylate group and are characterized as unsaturated or saturated depending upon whether a double bond is present in the hydrocarbon chain. Therefore, an unsaturated fatty acid has at least one double bond in its hydrocarbon chain whereas a saturated fatty acid has no double bonds in its fatty acid chain. Preferably, the acid is saturated.

In one embodiment, a fatty acid used to make the fatty acid monoalcohol esters is derived from natural sources such as, for example, beef tallow oil, lard oil, palm oil, castor oil, cottonseed oil, corn oil, peanut oil, soybean oil, sunflower oil, olive oil, whale oil, menhaden oil, sardine oil, coconut oil, palm kernel oil, babassu oil, rape oil, soya oil and the like and mixtures thereof. In one embodiment, a fatty acid used to make the fatty acid monoalcohol esters is an unsaturated fatty acid including, by way of example, myristoleic acid, palmitoleic acid, oleic acid, linolenic acid, and the like and mixtures thereof. In one embodiment, a fatty acid used to make the fatty acid monoalcohol ester is a saturated fatty acid including, by way of example, include caproic acid, caprylic acid, capric acid, lauric acid, myristic acid, palmitic acid, stearic acid, arachidic acid, behenic acid, lignoceric acid, and the like and mixtures thereof.

In one embodiment, a fatty acid used to make the fatty acid monoalcohol esters can vary depending on the desired fatty acid ester, but can include butyric, caproic, caprylic, capric, decenoic, lauric, cis-9-dodecenoic, myristic, myristoleic, cis-9-tetradecenoic, pentadecanoic, palmitic, palmitoleic, cis-9-hexadecenoic, heptadecanoic, heptadecenoic, stearic, oleic, linoleic, linolenic, ricinoleic, dihydroxystearic, nonadecanoic, arachidic, cis-9, cis-11-eicosenoic, eicosadienoic, eicosatrienoic, arachidonic, eicosapentaenoic, behenic, erucic, docosadienoic, 4,8,12,15,19-docosapentaenoic, docosahexaenoic, lignoceric, tetracosenoic and the like and mixtures thereof.

Suitable monoalcohols used to make the fatty acid monoalcohol esters include $C_1$ to $C_{20}$ linear or branched monoalcohols or $C_1$ to $C_{12}$ linear or branched monoalcohols. Examples of such monoalcohols include, but are not limited to, methanol, ethanol, propanol, propan-2-ol, isopropanol, butanol, sec-butanol, tert-butanol, 2-ethyl-hexanol, and the like.

In one embodiment, the ester will be a fatty acid methyl ester or mixture of fatty acid methyl esters, e.g., where the fatty acid of the ester is a fatty acid derived from coconut oil and the monoalcohol of the ester is methanol, although any monoalcohol ester or mixtures thereof of the above-described materials can be used, e.g., where the fatty acid of the ester is a fatty acid derived from coconut oil and the monoalcohol of the ester is one or more of methanol, ethanol, propanol, etc.

The $C_4$ to about $C_{75}$ fatty acid monoalcohol esters used in the method of the present invention can be obtained by methods known in the art or are commercially available from such sources as, for example, Cognis Corporation under the tradename Aqnique, e.g. Agnique ME 12-18-U.

In one embodiment, the fatty acid esters which may be employed include glyceryl tri-laurate, glyceryl tri-stearate, glyceryl tri-palmitate, glyceryl di-laurate, glyceryl mono-stearate, ethylene glycol di-laurate, pentaerythritol tetra-stearate, pentaerythritol tri-laurate, sorbitol mono-palmitate, sorbitol penta-stearate, propylene glycol mono-stearate.

In one embodiment, the alkanolamine includes, but is not limited to, monoalkanolamine and dialkanolamine. For example, the monoalkanolamine or dialkanolamine includes, but is not limited to, ethanolamine, diethanolamine, propanolamine, isopropanolamine, dipropanolamine, di-isopropanolamine, butanolamine, etc.

In one embodiment, the alkanolamide includes, but is not limited to, monoalkanolamide and dialkanolamide. For example, the monoalkanolamidne or dialkanolamidne includes, but is not limited to, ethanolamide, diethanolamide, propanolamide, isopropanolamide, dipropanolamide, di-isopropanolamide, butanolamide, etc.

The reaction to form the initial alkanolamide may be effected by heating the fatty acid ester and the amine in equivalent quantities to produce the desired product. Reaction may typically be effected by maintaining the reactants at a temperature of from about 100° C. to 200° C., and preferably from about 120° C. to about 150° C. for about 1 to about 10 hours, and preferably about 4 hours. The reaction can be solvent-free or carried out in a solvent, preferably one which is compatible with the ultimate composition in which the product is to be used.

In one embodiment the molar ratio of fatty acid ester to mono- or dialkanolamine reactants is chosen to minimize the amount of free mono- or dialkanolamine reactant in the reaction product. Typically, a ratio of fatty acid ester to mono- or dialkanolamine reactants of about 1:1 to about 2:1 is preferred, especially an approximately equimolar ratio.

In one embodiment the amide reaction product is selected from the group consisting of N,N-bis(2-hydroxyethyl)dodecanamide, N,N-bis(2-hydroxyethyl)oleamide, N,N-bis(2 hydroxyethyl)stearamide, N,N-bis(2-hydroxypropyl)dodecanamide, and N-(2-hydroxyethyl)dodecanamide.

In one embodiment, the aging temperature is from 70° C. to 100° C., preferably from 70° C. to 90° C., preferably from 70° C. to 85° C., preferably from 75° C. to 85° C., preferably from 75° C. to 80° C., preferably from 80° C. to 85° C., and preferably 80° C.

In one embodiment, the aging time is from 10 to 112 hours, preferably from 10 to 96 hours, preferably from 10 to 50 hours, preferably from 20 to 96 hours, preferably from 30 to 96 hours, preferably from 30 to 50 hours, preferably from 40 to 96 hours, preferably from 50 to 96 hours, preferably from 60 to 96 hours, preferably from 70 to 96 hours, preferably from 80 to 96 hours, preferably from 90 to 96 hours, and preferably 96 hours.

In one embodiment, the ratio of alkanolamide to ester (i.e., both ester amine reaction product and fatty acid alkyl ester) is at least 0.1:1.0, at least 0.1:1.0 to 12:1, at least 0.2:1.0 to 11:1, at least 0.2:1.0 to 10:1, at least 0.2:1.0 to 8:1, at least 0.2:1.0 to 6:1, at least 0.2:1.0 to 4:1, or at least 0.2:1.0 to 2:1.

In one embodiment, the percent reduction in alkanolamine is from 20 to 70%, preferably from 25 to 65%, preferably from 25 to 60%, preferably from 25 to 55%, preferably from 25 to 50%, preferably from 25 to 45%, preferably from 25 to 40%, and preferably from 25 to 30%.

In one embodiment, the ratio of amide reaction product to ester reaction product is increased by at least 5%, at least 10%, at least 15%, at least 20%, at least 25%, at least 30%, at least 40%, at least 50%, at least 60%, at least 70%, at least 80%, at least 90%, at least 100%, at least 110%, at least 120%, at least 130%, at least 140%, at least 150%, at least 200%, at least 250%, at least 300%, at least 350%, or at least 400%.

In one embodiment, when the alkanolamine is diethanolamine, the amount of 1,4-Bis(2-hydroxyethyl) piperazine present in the mixture is maintained below 0.4 wt %, or below 0.3 wt %, or below 0.2 wt %, or below 0.1 wt %.

In many instances, it may be advantageous to form concentrates of the lubricating oil soluble additive composition of the present invention within a carrier liquid, or concentrates of the liquid hydrocarbon fuel additive composition of the present invention within a carrier liquid. These additive concentrates provide a convenient method of handling, transporting, and ultimately blending into lubricant base oils to provide a finished lubricant or into fuels to provide a finished fuel.

Generally, the lubricating oil soluble additive concentrates of the invention are not useable or suitable as finished lubricants or finished fuels on their own. Rather, the lubricating oil soluble additive concentrates can be blended with lubricant base oil stocks to provide a finished lubricant. It is desired that the carrier liquid readily solubilizes the lubricating oil soluble additive of the invention and provides an oil additive concentrate that is readily soluble in the lubricant base oil stocks or fuels. In addition, it is desired that the carrier liquid not introduce any undesirable characteristics, including, for example, high volatility, high viscosity, and impurities such as heteroatoms, to the lubricant base oil stocks and thus, ultimately to the finished lubricant or fuel. The present invention therefore further provides an oil soluble additive concentrate composition comprising an inert carrier fluid and from 2.0% to 90% by weight, based on the total concentrate, of an oil soluble additive composition according to the invention. The inert carrier fluid may be a lubricating oil or a suitable hydrocarbon solvent.

These concentrates usually contain from about 2.0% to about 90% by weight, preferably 10% to 50% by weight of the oil soluble additive composition of this invention and may contain, in addition, one or more other additives known in the art and described below. The remainder of the concentrate is the substantially inert carrier liquid or suitable hydrocarbon solvent.

The Oil of Lubricating Viscosity

The lubricating oil compositions disclosed herein generally comprise at least one oil of lubricating viscosity. Any base oil known to a skilled artisan can be used as the oil of lubricating viscosity disclosed herein. Some base oils suitable for preparing the lubricating oil compositions have been described in Mortier et al., "*Chemistry and Technology of Lubricants,*" 2nd Edition, London, Springer, Chapters 1 and 2 (1996); and A. Sequeria, Jr., "*Lubricant Base Oil and Wax Processing,*" New York, Marcel Decker, Chapter 6, (1994); and D. V. Brock, *Lubrication Engineering*, Vol. 43, pages 184-5, (1987), all of which are incorporated herein by reference. Generally, the amount of the base oil in the lubricating oil composition may be from about 70 to about 99.5 wt. %, based on the total weight of the lubricating oil composition. In some embodiments, the amount of the base oil in the lubricating oil composition is from about 75 to about 99 wt. %, from about 80 to about 98.5 wt. %, or from about 80 to about 98 wt. %, based on the total weight of the lubricating oil composition.

In certain embodiments, the base oil is or comprises any natural or synthetic lubricating base oil fraction. Some non-limiting examples of synthetic oils include oils, such as polyalphaolefins or PAOs, prepared from the polymerization of at least one alpha-olefin, such as ethylene, or from hydrocarbon synthesis procedures using carbon monoxide and hydrogen gases, such as the Fisher-Tropsch process. In certain embodiments, the base oil comprises less than about 10 wt. % of one or more heavy fractions, based on the total weight of the base oil. A heavy fraction refers to a lube oil fraction having a viscosity of at least about 20 cSt at 100° C. In certain embodiments, the heavy fraction has a viscosity of at least about 25 cSt or at least about 30 cSt at 100° C. In further embodiments, the amount of the one or more heavy fractions in the base oil is less than about 10 wt. %, less than about 5 wt. %, less than about 2.5 wt. %, less than about 1 wt. %, or less than about 0.1 wt. %, based on the total weight of the base oil. In still further embodiments, the base oil comprises no heavy fraction.

In certain embodiments, the lubricating oil compositions comprise a major amount of a base oil of lubricating viscosity. In some embodiments, the base oil has a kinematic viscosity at 100° C. from about 2.5 centistokes (cSt) to about 20 cSt, from about 5 centistokes (cSt) to about 20 cSt, from about 7 cSt to about 16 cSt, or from about 9 cSt to about 15 cSt. The kinematic viscosity of the base oils or the lubricating oil compositions disclosed herein can be measured according to ASTM D 445, which is incorporated herein by reference.

In other embodiments, the base oil is or comprises a base stock or blend of base stocks. In further embodiments, the base stocks are manufactured using a variety of different processes including, but not limited to, distillation, solvent refining, hydrogen processing, oligomerization, esterification, and rerefining. In some embodiments, the base stocks comprise a rerefined stock. In further embodiments, the rerefined stock shall be substantially free from materials introduced through manufacturing, contamination, or previous use.

In some embodiments, the base oil comprises one or more of the base stocks in one or more of Groups I-V as specified in the American Petroleum Institute (API) Publication 1509, Fourteen Edition, December 1996 (i.e., API Base Oil Interchangeability Guidelines for Passenger Car Motor Oils and Diesel Engine Oils), which is incorporated herein by reference. The API guideline defines a base stock as a lubricant component that may be manufactured using a variety of different processes. Groups I, II and III base stocks are mineral oils, each with specific ranges of the amount of saturates, sulfur content and viscosity index. Group IV base stocks are polyalphaolefins (PAO). Group V base stocks include all other base stocks not included in Group I, II, III, or IV.

The saturates levels, sulfur levels and viscosity indices for Group I, II and III base stocks are listed in Table 1 below.

TABLE 1

| Group | Saturates (As determined by ASTM D 2007) | Sulfur (As determined by ASTM D 2270) | Viscosity Index (As determined by ASTM D 4294, ASTM D 4297 or ASTM D 3120) |
|---|---|---|---|
| I | Less than 90% saturates. | Greater than or equal to 0.03% sulfur. | Greater than or equal to 80 and less than 120. |
| II | Greater than or equal to 90% saturates. | Less than 0.03% sulfur. | Greater than or equal to 80 and less than 120. |
| III | Greater than or equal to 90% saturates. | Less than or equal to 0.03% sulfur. | Greater than or equal to 120. |

In some embodiments, the base oil comprises one or more of the base stocks in Group I, II, III, IV, V or a combination thereof. In other embodiments, the base oil comprises one or more of the base stocks in Group II, III, IV or a combination thereof. In further embodiments, the base oil comprises one or more of the base stocks in Group II, III, IV or a combination thereof wherein the base oil has a kinematic viscosity from about 5 centistokes (cSt) to about 20 cSt, from about 7 cSt to about 16 cSt, or from about 9 cSt to about 15 cSt at 100° C.

The base oil may be selected from the group consisting of natural oils of lubricating viscosity, synthetic oils of lubricating viscosity and mixtures thereof. In some embodiments, the base oil includes base stocks obtained by isomerization of synthetic wax and slack wax, as well as hydrocrackate base stocks produced by hydrocracking (rather than solvent extracting) the aromatic and polar components of the crude. In other embodiments, the base oil of lubricating viscosity includes natural oils, such as animal oils, vegetable oils, mineral oils, oils derived from coal or shale, and combinations thereof. Some non-limiting examples of animal oils include bone oil, lanolin, fish oil, lard oil, dolphin oil, seal oil, shark oil, tallow oil, and whale oil. Some non-limiting examples of vegetable oils include castor oil, olive oil, peanut oil, rapeseed oil, corn oil, sesame oil, cottonseed oil, soybean oil, sunflower oil, safflower oil, hemp oil, linseed oil, tung oil, oiticica oil, jojoba oil, and meadow foam oil. Such oils may be partially or fully hydrogenated. Some non-limiting examples of mineral oils include Groups I, II, and III base stocks, liquid petroleum oils and solvent treated or acid-treated mineral oils of the paraffinic, naphthenic or mixed paraffinic-naphthenic types. In some embodiments, the mineral oils are neat or low viscosity mineral oils.

In some embodiments, the synthetic oils of lubricating viscosity include hydrocarbon oils and halo-substituted hydrocarbon oils such as polymerized and inter-polymerized olefins, alkylbenzenes, polyphenyls, alkylated diphenyl ethers, alkylated diphenyl sulfides, as well as their derivatives, analogues and homologues thereof, and the like. In other embodiments, the synthetic oils include alkylene oxide polymers, interpolymers, copolymers and derivatives thereof wherein the terminal hydroxyl groups can be modified by esterification, etherification, and the like. In further embodiments, the synthetic oils include the esters of dicarboxylic acids with a variety of alcohols. In certain embodiments, the synthetic oils include esters made from $C_5$ to $C_{12}$ monocarboxylic acids and polyols and polyol ethers. In further embodiments, the synthetic oils include tri-alkyl phosphate ester oils, such as tri-n-butyl phosphate and tri-iso-butyl phosphate.

In some embodiments, the synthetic oils of lubricating viscosity include silicon-based oils (such as the polyalkyl-, polyaryl-, polyalkoxy-, polyaryloxy-siloxane oils and silicate oils). In other embodiments, the synthetic oils include liquid esters of phosphorus-containing acids, polymeric tetrahydrofurans, polyalphaolefins, and the like.

Base oil derived from the hydroisomerization of wax may also be used, either alone or in combination with the aforesaid natural and/or synthetic base oil. Such wax isomerate oil is produced by the hydroisomerization of natural or synthetic waxes or mixtures thereof over a hydroisomerization catalyst.

In further embodiments, the base oil comprises a poly-alpha-olefin (PAO). In general, the poly-alpha-olefins may be derived from an alpha-olefin having from about 2 to about 30, from about 4 to about 20, or from about 6 to about 16 carbon atoms. Non-limiting examples of suitable poly-alpha-olefins include those derived from octene, decene, mixtures thereof, and the like. These poly-alpha-olefins may have a viscosity from about 2 to about 15, from about 3 to about 12, or from about 4 to about 8 centistokes at 100° C. In some instances, the poly-alpha-olefins may be used together with other base oils such as mineral oils.

In further embodiments, the base oil comprises a polyalkylene glycol or a polyalkylene glycol derivative, where the terminal hydroxyl groups of the polyalkylene glycol may be modified by esterification, etherification, acetylation and the like. Non-limiting examples of suitable polyalkylene glycols include polyethylene glycol, polypropylene glycol, polyisopropylene glycol, and combinations thereof. Non-limiting examples of suitable polyalkylene glycol derivatives include ethers of polyalkylene glycols (e.g., methyl ether of polyisopropylene glycol, diphenyl ether of polyethylene glycol, diethyl ether of polypropylene glycol, etc.), mono- and polycarboxylic esters of polyalkylene glycols, and combinations thereof. In some instances, the polyalkylene glycol or polyalkylene glycol derivative may be used together with other base oils such as poly-alpha-olefins and mineral oils.

In further embodiments, the base oil comprises any of the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, and the like) with a variety of alcohols (e.g., butyl alcohol, hexyl alcohol, dodecyl alcohol, 2-ethylhexyl alcohol, ethylene glycol, diethylene glycol monoether, propylene glycol, and the like). Non-limiting examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the like.

In further embodiments, the base oil comprises a hydrocarbon prepared by the Fischer-Tropsch process. The Fischer-Tropsch process prepares hydrocarbons from gases containing hydrogen and carbon monoxide using a Fischer-Tropsch catalyst. These hydrocarbons may require further processing in order to be useful as base oils. For example, the hydrocarbons may be dewaxed, hydroisomerized, and/or hydrocracked using processes known to a person of ordinary skill in the art.

In further embodiments, the base oil comprises an unrefined oil, a refined oil, a rerefined oil, or a mixture thereof. Unrefined oils are those obtained directly from a natural or synthetic source without further purification treatment. Non-limiting examples of unrefined oils include shale oils obtained directly from retorting operations, petroleum oils obtained directly from primary distillation, and ester oils obtained directly from an esterification process and used without further treatment. Refined oils are similar to the unrefined oils except the former have been further treated by one or more purification processes to improve one or more properties. Many such purification processes are known to those skilled in the art such as solvent extraction, secondary distillation, acid or base extraction, filtration, percolation, and the like. Rerefined oils are obtained by applying to refined oils processes similar to those used to obtain refined oils. Such rerefined oils are also known as reclaimed or reprocessed oils and often are additionally treated by processes directed to removal of spent additives and oil breakdown products.

Additional Lubricating Oil Additives

Optionally, the lubricating oil composition of the present invention may further comprise at least an additive or a modifier (hereinafter designated as "additive") that can impart or improve any desirable property of the lubricating oil composition. Any additive known to a person of ordinary skill in the art may be used in the lubricating oil compositions disclosed herein. Some suitable additives have been described in Mortier et al., "*Chemistry and Technology of Lubricants,*" 2nd Edition, London, Springer, (1996); and Leslie R. Rudnick, "*Lubricant Additives: Chemistry and Applications*," New York, Marcel Dekker (2003), both of which are incorporated herein by reference.

In some embodiments, the additive can be selected from the group consisting of antioxidants, antiwear agents, detergents, rust inhibitors, demulsifiers, friction modifiers, multifunctional additives, viscosity index improvers, pour point depressants, foam inhibitors, metal deactivators, dispersants, corrosion inhibitors, lubricity improvers, thermal stability improvers, anti-haze additives, icing inhibitors, dyes, markers, static dissipaters, biocides and combinations thereof. A variety of the additives are known and commercially available. These additives, or their analogous compounds, may be employed for the preparation of the lubricating oil compositions of the invention by the usual blending procedures.

Examples of antioxidants include, but are not limited to, aminic types, e.g., diphenylamine, phenyl-alpha-napthylamine, N,N-di(alkylphenyl) amines; and alkylated phenylene-diamines; phenolics such as, for example, BHT, sterically hindered alkyl phenols such as 2,6-di-tert-butyl-phenol, 2,6-di-tert-butyl-p-cresol and 2,6-di-tert-butyl-4-(2-octyl-3-propanoic) phenol; and mixtures thereof.

Examples of antiwear agents include, but are not limited to, zinc dialkyldithiophosphates and zinc diaryldithiophosphates, e.g., those described in an article by Born et al. entitled "Relationship between Chemical Structure and Effectiveness of some Metallic Dialkyl- and Diaryl-dithiophosphates in Different Lubricated Mechanisms", appearing in Lubrication Science 4-2 Jan. 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Representative examples of ashless dispersants include, but are not limited to, amines, alcohols, amides, or ester polar moieties attached to a polymer backbone via bridging groups. An ashless dispersant of the present invention may be, for example, selected from oil soluble salts, esters, amino-esters, amides, imides, and oxazolines of long chain hydrocarbon substituted mono and dicarboxylic acids or their anhydrides; thiocarboxylate derivatives of long chain hydrocarbons, long chain aliphatic hydrocarbons having a polyamine attached directly thereto; and Mannich condensation products formed by condensing a long chain substituted phenol with formaldehyde and polyalkylene polyamine.

Carboxylic dispersants are reaction products of carboxylic acylating agents (acids, anhydrides, esters, etc.) comprising at least about 34 and preferably at least about 54 carbon atoms with nitrogen containing compounds (such as amines), organic hydroxy compounds (such as aliphatic compounds including monohydric and polyhydric alcohols, or aromatic compounds including phenols and naphthols), and/or basic inorganic materials. These reaction products include imides, amides, esters, and salts.

Succinimide dispersants are a type of carboxylic dispersant. They are produced by reacting hydrocarbyl-substituted succinic acylating agent with organic hydroxy compounds, or with amines comprising at least one hydrogen atom attached to a nitrogen atom, or with a mixture of the hydroxy compounds and amines. The term "succinic acylating agent" refers to a hydrocarbon-substituted succinic acid or a succinic acid-producing compound, the latter encompasses the acid itself. Such materials typically include hydrocarbyl-substituted succinic acids, anhydrides, esters (including half esters) and halides.

Succinic-based dispersants have a wide variety of chemical structures. One class of succinic-based dispersants may be represented by Formula 7:

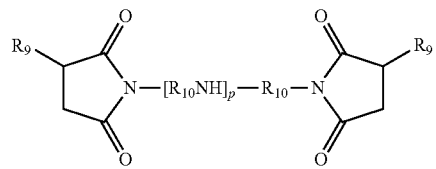

Formula 7 wherein each $R_9$ is independently a hydrocarbyl group, such as a polyolefin-derived group. Typically the hydrocarbyl group is an alkenyl group, such as a polyisobutenyl group. Alternatively expressed, the $R_9$ groups can contain about 40 to about 500 carbon atoms, and these atoms may be present in aliphatic forms. $R_{10}$ is an alkylene group, commonly an ethylene ($C_2H_4$) group; and p is 1 to 11. Examples of succinimide dispersants include those described in, for example, U.S. Pat. Nos. 3,172,892, 4,234, 435 and 6,165,235.

The polyalkenes from which the substituent groups are derived are typically homopolymers and interpolymers of polymerizable olefin monomers of 2 to about 16 carbon atoms, and usually 2 to 6 carbon atoms. The amines which are reacted with the succinic acylating agents to form the carboxylic dispersant composition can be monoamines or polyamines.

Succinimide dispersants are referred to as such since they normally contain nitrogen largely in the form of imide functionality, although the nitrogen functionality may be in the form of amines, amine salts, amides, imidazolines as well as mixtures thereof. To prepare a succinimide dispersant, one or more succinic acid-producing compounds and one or more amines are heated and typically water is removed, optionally in the presence of a substantially inert organic liquid solvent/diluent. The reaction temperature can range from about 80° C. up to the decomposition temperature of the mixture or the product, which typically falls between about 100° C. to about 300° C. Additional details and examples of procedures for preparing the succinimide dispersants of the present invention include those described in, for example, U.S. Pat. Nos. 3,172,892, 3,219,666, 3,272, 746, 4,234,435, 6,165,235 and 6,440,905.

Suitable ashless dispersants may also include amine dispersants, which are reaction products of relatively high molecular weight aliphatic halides and amines, preferably polyalkylene polyamines. Examples of such amine dispersants include those described in, for example, U.S. Pat. Nos. 3,275,554, 3,438,757, 3,454,555 and 3,565,804.

Suitable ashless dispersants may further include "Mannich dispersants," which are reaction products of alkyl phenols in which the alkyl group contains at least about 30 carbon atoms with aldehydes (especially formaldehyde) and amines (especially polyalkylene polyamines). Examples of such dispersants include those described in, for example, U.S. Pat. Nos. 3,036,003, 3,586,629. 3,591,598 and 3,980, 569.

Suitable ashless dispersants may also be post-treated ashless dispersants such as post-treated succinimides, e.g., post-treatment processes involving borate or ethylene carbonate as disclosed in, for example, U.S. Pat. Nos. 4,612, 132 and 4,746,446; and the like as well as other post-treatment processes. The carbonate-treated alkenyl succinimide is a polybutene succinimide derived from polybutenes having a molecular weight of about 450 to about 3000, preferably from about 900 to about 2500, more preferably from about 1300 to about 2400, and most preferably from about 2000 to about 2400, as well as mixtures of these molecular weights.

An ashless dispersant can be prepared by reacting, under reactive conditions, a mixture of a polybutene succinic acid derivative, an unsaturated acidic reagent copolymer of an unsaturated acidic reagent and an olefin, and a polyamine, such as disclosed in U.S. Pat. No. 5,716,912, the contents of which are incorporated herein by reference.

Suitable ashless dispersants may also be polymeric, which are interpolymers of oil-solubilizing monomers such as decyl methacrylate, vinyl decyl ether and high molecular weight olefins with monomers containing polar substituents. Examples of polymeric dispersants include those described in, for example, U.S. Pat. Nos. 3,329,658; 3,449,250 and 3,666,730.

Generally, the one or more ashless dispersants are present in the lubricating oil composition in an amount ranging from about 0.01 wt. % to about 10 wt. %, based on the total weight of the lubricating oil composition.

Representative examples of metal detergents include sulfonates, alkylphenates, sulfurized alkyl phenates, carboxylates, salicylates, phosphonates, and phosphinates. Commercial products are generally referred to as neutral or overbased. Overbased metal detergents are generally produced by carbonating a mixture of hydrocarbons, detergent acid, for example: sulfonic acid, alkylphenol, carboxylate etc., metal oxide or hydroxides (for example calcium oxide or calcium hydroxide) and promoters such as xylene, methanol and water. For example, for preparing an overbased calcium sulfonate, in carbonation, the calcium oxide or hydroxide reacts with the gaseous carbon dioxide to form calcium carbonate. The sulfonic acid is neutralized with an excess of CaO or Ca(OH)$_2$, to form the sulfonate.

Other examples of suitable detergents include borated sulfonates. In general, a borated sulfonate for use herein can be any borated sulfonate known in the art. A borated sulfonate for use herein can have a total base number (TBN) of from about 10 to about 500. In one embodiment, a borated sulfonate has a TBN is from about 10 to about 100. In one embodiment, a borated sulfonate has a TBN is from about 100 to about 250. In one embodiment, a borated sulfonate has a TBN of from about 250 to about 500.

The borated alkaline earth metal sulfonates can be prepared by methods known in the art, e.g., as disclosed in U.S. Patent Application Publication No. 20070123437, the contents of which are incorporated by reference herein. For example, the borated alkaline earth metal sulfonate is prepared in the following manner: (a) reacting (i) at least one of an oil soluble sulfonic acid or alkaline earth sulfonate salt or mixtures thereof; (ii) at least one source of an alkaline earth metal; and (iii) at least one source of boron, in the presence of (iv) at least one hydrocarbon solvent; and (v) from 0 to less than 10 mole percent, relative to the source of boron, of an overbasing acid, other than the source of boron; and (b) heating the reaction product of (a) to a temperature above the distillation temperature of (iv) to distill (iv) and water of reaction.

Metal-containing or ash-forming detergents function as both detergents to reduce or remove deposits and as acid neutralizers or rust inhibitors, thereby reducing wear and corrosion and extending engine life. Detergents generally comprise a polar head with a long hydrophobic tail. The polar head comprises a metal salt of an acidic organic compound. The salts may contain a substantially stoichiometric amount of the metal in which case they are usually described as normal or neutral salts, and would typically have a total base number or TBN (as can be measured by ASTM D2896) of from 0 to about 80. A large amount of a metal base may be incorporated by reacting excess metal compound (e.g., an oxide or hydroxide) with an acidic gas (e.g., carbon dioxide). The resulting overbased detergent comprises neutralized detergent as the outer layer of a metal base (e.g., carbonate) micelle. Such overbased detergents may have a TBN of about 150 or greater, and typically will have a TBN of from about 250 to about 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., barium, sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from about 20 to about 450, neutral and overbased calcium phenates and sulfurized phenates having TBN of from about 50 to about 450 and neutral and overbased magnesium or calcium salicylates having a TBN of from about 20 to about 450. Combinations of detergents, whether overbased or neutral or both, may be used.

In one embodiment, the detergent can be one or more alkali or alkaline earth metal salts of an alkyl-substituted hydroxyaromatic carboxylic acid. Suitable hydroxyaromatic compounds include mononuclear monohydroxy and polyhydroxy aromatic hydrocarbons having 1 to 4, and preferably 1 to 3, hydroxyl groups. Suitable hydroxyaromatic compounds include phenol, catechol, resorcinol, hydroquinone, pyrogallol, cresol, and the like. The preferred hydroxyaromatic compound is phenol.

The alkyl substituted moiety of the alkali or alkaline earth metal salt of an alkyl-substituted hydroxyaromatic carboxylic acid is derived from an alpha olefin having from about 10 to about 80 carbon atoms. The olefins employed may be linear or branched. The olefin may be a mixture of linear olefins, a mixture of isomerized linear olefins, a mixture of branched olefins, a mixture of partially branched linear or a mixture of any of the foregoing.

In one embodiment, the mixture of linear olefins that may be used is a mixture of normal alpha olefins selected from olefins having from about 12 to about 30 carbon atoms per molecule. In one embodiment, the normal alpha olefins are isomerized using at least one of a solid or liquid catalyst.

In another embodiment, the olefins are a branched olefinic propylene oligomer or mixture thereof having from about 20 to about 80 carbon atoms, i.e., branched chain olefins derived from the polymerization of propylene. The olefins may also be substituted with other functional groups, such as hydroxy groups, carboxylic acid groups, heteroatoms, and the like. In one embodiment, the branched olefinic propylene oligomer or mixtures thereof have from about 20 to about 60 carbon atoms. In one embodiment, the branched olefinic propylene oligomer or mixtures thereof have from about 20 to about 40 carbon atoms.

In one embodiment, at least about 75 mole % (e.g., at least about 80 mole %, at least about 85 mole %, at least about 90 mole %, at least about 95 mole %, or at least about 99 mole %) of the alkyl groups contained within the alkali or alkaline earth metal salt of an alkyl-substituted hydroxyaromatic carboxylic acid such as the alkyl groups of an alkaline earth metal salt of an alkyl-substituted hydroxybenzoic acid detergent are a $C_{20}$ or higher. In another embodiment, the alkali or alkaline earth metal salt of an alkyl-substituted hydroxyaromatic carboxylic acid is an alkali or alkaline earth metal salt of an alkyl-substituted hydroxybenzoic acid that is derived from an alkyl-substituted hydroxybenzoic acid in which the alkyl groups are the residue of normal alpha-olefins containing at least 75 mole % $C_{20}$ or higher normal alpha-olefins.

In another embodiment, at least about 50 mole % (e.g., at least about 60 mole %, at least about 70 mole %, at least about 80 mole %, at least about 85 mole %, at least about 90 mole %, at least about 95 mole %, or at least about 99 mole %) of the alkyl groups contained within the alkali or alkaline earth metal salt of an alkyl-substituted hydroxyaromatic carboxylic acid such as the alkyl groups of an alkali or alkaline earth metal salt of an alkyl-substituted hydroxybenzoic acid are about $C_{14}$ to about $C_{18}$.

The resulting alkali or alkaline earth metal salt of an alkyl-substituted hydroxyaromatic carboxylic acid will be a mixture of ortho and para isomers. In one embodiment, the product will contain about 1 to 99% ortho isomer and 99 to 1% para isomer. In another embodiment, the product will contain about 5 to 70% ortho and 95 to 30% para isomer.

The alkali or alkaline earth metal salts of an alkyl-substituted hydroxyaromatic carboxylic acid can be neutral or overbased. Generally, an overbased alkali or alkaline earth metal salt of an alkyl-substituted hydroxyaromatic carboxylic acid is one in which the TBN of the alkali or alkaline earth metal salts of an alkyl-substituted hydroxyaromatic carboxylic acid has been increased by a process such as the addition of a base source (e.g., lime) and an acidic overbasing compound (e.g., carbon dioxide).

Overbased salts may be low overbased, e.g., an overbased salt having a TBN below about 100. In one embodiment, the TBN of a low overbased salt may be from about 5 to about 50. In another embodiment, the TBN of a low overbased salt may be from about 10 to about 30. In yet another embodiment, the TBN of a low overbased salt may be from about 15 to about 20.

Overbased detergents may be medium overbased, e.g., an overbased salt having a TBN from about 100 to about 250. In one embodiment, the TBN of a medium overbased salt may be from about 100 to about 200. In another embodiment, the TBN of a medium overbased salt may be from about 125 to about 175.

Overbased detergents may be high overbased, e.g., an overbased salt having a TBN above about 250. In one embodiment, the TBN of a high overbased salt may be from about 250 to about 450.

Sulfonates may be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl or their halogen derivatives. The alkylation may be carried out in the presence of a catalyst with alkylating agents having from about 3 to more than 70 carbon atoms. The alkaryl sulfonates usually contain from about 9 to about 80 or more carbon atoms, preferably from about 16 to about 60 carbon atoms per alkyl substituted aromatic moiety.

The oil soluble sulfonates or alkaryl sulfonic acids may be neutralized with oxides, hydroxides, alkoxides, carbonates, carboxylate, sulfides, hydrosulfides, nitrates and borates. The amount of metal compound is chosen having regard to the desired TBN of the final product but typically ranges from about 100 to about 220 wt. % (preferably at least about 125 wt. %) of that stoichiometrically required.

Metal salts of phenols and sulfurized phenols are prepared by reaction with an appropriate metal compound such as an oxide or hydroxide and neutral or overbased products may be obtained by methods well known in the art. Sulfurized phenols may be prepared by reacting a phenol with sulfur or a sulfur containing compound such as hydrogen sulfide, sulfur monohalide or sulfur dihalide, to form products which are generally mixtures of compounds in which 2 or more phenols are bridged by sulfur containing bridges.

Generally, the one or more detergents are present in the lubricating oil composition in an amount ranging from about 0.01 wt. % to about 10 wt. %, based on the total weight of the lubricating oil composition.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are herein incorporated by reference.

Examples of antifoaming agents include, but are not limited to, polymers of alkyl methacrylate; polymers of dimethylsilicone and the like and mixtures thereof.

Examples of a pour point depressant include, but are not limited to, polymethacrylates, alkyl acrylate polymers, alkyl methacrylate polymers, di (tetra-paraffin phenol) phthalate, condensates of tetra-paraffin phenol, condensates of a chlorinated paraffin with naphthalene and combinations thereof. In one embodiment, a pour point depressant comprises an ethylene-vinyl acetate copolymer, a condensate of chlorinated paraffin and phenol, polyalkyl styrene and the like and combinations thereof. The amount of the pour point depressant may vary from about 0.01 wt. % to about 10 wt. %.

Examples of a demulsifier include, but are not limited to, anionic surfactants (e.g., alkyl-naphthalene sulfonates, alkyl benzene sulfonates and the like), nonionic alkoxylated alkylphenol resins, polymers of alkylene oxides (e.g., polyethylene oxide, polypropylene oxide, block copolymers of ethylene oxide, propylene oxide and the like), esters of oil soluble acids, polyoxyethylene sorbitan ester and the like and combinations thereof. The amount of the demulsifier may vary from about 0.01 wt. % to about 10 wt. %.

Examples of a corrosion inhibitor include, but are not limited to, half esters or amides of dodecylsuccinic acid, phosphate esters, thiophosphates, alkyl imidazolines, sarcosines and the like and combinations thereof. The amount of the corrosion inhibitor may vary from about 0.01 wt. % to about 5 wt. %.

Examples of an extreme pressure agent include, but are not limited to, sulfurized animal or vegetable fats or oils, sulfurized animal or vegetable fatty acid esters, fully or partially esterified esters of trivalent or pentavalent acids of phosphorus, sulfurized olefins, dihydrocarbyl polysulfides, sulfurized Diels-Alder adducts, sulfurized dicyclopentadiene, sulfurized or co-sulfurized mixtures of fatty acid esters and monounsaturated olefins, co-sulfurized blends of fatty acid, fatty acid ester and alpha-olefin, functionally-substituted dihydrocarbyl polysulfides, thia-aldehydes, thia-ketones, epithio compounds, sulfur-containing acetal derivatives, co-sulfurized blends of terpene and acyclic olefins, and polysulfide olefin products, amine salts of phosphoric acid esters or thiophosphoric acid esters and the like and combinations thereof. The amount of the extreme pressure agent may vary from about 0.01 wt. % to about 5 wt. %.

Each of the foregoing additives, when used, is used at a functionally effective amount to impart the desired properties to the lubricant. Thus, for example, if an additive is a friction modifier, a functionally effective amount of this friction modifier would be an amount sufficient to impart the desired friction modifying characteristics to the lubricant. Generally, the concentration of each of these additives, when used, may range, unless otherwise specified, from about 0.001 wt. % to about 10 wt. %, in one embodiment from about 0.005 wt. % to about 5 wt. %, or in one embodiment from about 0.1 wt. % to about 2.5 wt. %, based on the total weight of the lubricating oil composition. Further, the total amount of the additives in the lubricating oil composition may range from about 0.001 wt. % to about 20 wt. %, from about 0.01 wt. % to about 10 wt. %, or from about 0.1 wt. % to about 5 wt. %, based on the total weight of the lubricating oil composition.

The final application of the lubricating oil compositions or fuel additive compositions of the present invention may be, for example, in railroads engines and the like, marine cylinder lubricants in crosshead diesel engines, crankcase lubricants, in automobiles, lubricants for heavy machinery such as steel mills and the like, or as greases for bearings and the like. Whether the lubricating oil composition or fuel additive composition is fluid or solid will ordinarily depend on whether a thickening agent is present. Typical thickening agents include polyurea acetates, lithium stearate and the like.

The resulting mono- or dialkanol amide produced by the method of the invention can be used to provide a decrease in friction in an internal combustion engine, e.g., a spark-ignition engine or compression-ignition engine, through its use as a fuel or lubricant additive. In one embodiment, the resulting mono- or dialkanol amide produced by the methods of the invention will be employed in a friction-modifying or lubricity effective amount in a fuel composition containing a major amount of a liquid hydrocarbon fuel. The fuel can be any internal combustion engine hydrocarbon fuel, e.g., diesel, gasoline, jet fuels, etc.; alcoholic fuels such as methanol or ethanol; or a mixture of any of the foregoing.

When the fuel is diesel, such fuel generally boils above about 212° F. The diesel fuel can comprise atmospheric distillate or vacuum distillate, or a blend in any proportion of straight run and thermally and/or catalytically cracked distillates. Preferred diesel fuels have a cetane number of at least 40, preferably above 45, and more preferably above 50. The diesel fuel can have such cetane numbers prior to the addition of any cetane improver. The cetane number of the fuel can be raised by the addition of a cetane improver.

When the fuel is gasoline, it can be derived from straight-chain naphtha, polymer gasoline, natural gasoline, catalytically cracked or thermally cracked hydrocarbons, catalytically reformed stocks, etc. It will be understood by one skilled in the art that gasoline fuels typically boil in the range of about 80° to 450° F. and can contain straight chain or branched chain paraffins, cycloparaffins, olefins, aromatic hydrocarbons, and any mixture of these.

Generally, the composition of the fuel is not critical and any conventional motor fuel base can be employed in the practice of this invention.

The proper concentration of the resulting mono- or dialkanol amide produced by the methods of the invention that is necessary to achieve the desired friction modification in the fuel composition is dependent upon a variety of factors including, for example, the type of fuel used, the presence of other additives, etc. Generally, however, the range of the resulting mono- or dialkanol amide concentration in the fuel composition is from about 10 to about 10,000 parts per million and preferably from about 30 to about 5000 parts per million of the additive per part of base fuel. If other friction modifiers are present, a lesser amount of the resulting mono- or dialkanol amide additive may be used.

The resulting mono- or dialkanol amide additive described herein may also be formulated as a fuel concentrate, using an inert stable oleophilic organic solvent boiling in the range of about 150° F. to about 400° F. In one embodiment, a suitable inert stable oleophilic organic solvent includes aliphatic or an aromatic hydrocarbon solvents, e.g., solvents such as benzene, toluene, xylene or higher-boiling aromatics or aromatic thinners. Aliphatic alcohols of about 3 to 8 carbon atoms, e.g., isopropanol, isobutylcarbinol, n-butanol and the like, in combination with hydrocarbon solvents are also suitable for use with the fuel additive. In the fuel concentrate, the amount of the additive will be ordinarily be about 5 or more wt. % and generally not exceed about 70 wt. %, preferably from about 5 wt. % to about 50 wt. % and more preferably from about 10 wt. % to about 25 wt. %.

In another embodiment of the invention, the lubricating oil compositions of the present invention may be provided as an additive package or concentrate in which the additive is incorporated into a substantially inert, normally liquid organic diluent such as, for example, mineral oil, naphtha, benzene, toluene or xylene to form an additive concentrate. These concentrates usually contain from about 20% to about 80% by weight of such diluent. Typically, a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. The additive package will also typically contain one or more of the various other additives, referred to above, in the desired amounts and ratios to facilitate direct combination with the requisite amount of base oil.

The following examples are presented to exemplify embodiments of the invention but are not intended to limit the invention to the specific embodiments set forth. Unless indicated to the contrary, all parts and percentages are by weight. All numerical values are approximate. When numerical ranges are given, it should be understood that embodiments outside the stated ranges may still fall within the scope of the invention. Specific details described in each example should not be construed as necessary features of the invention.

EXAMPLES

The following examples are intended for illustrative purposes only and do not limit in any way the scope of the present invention.

Example 1

General procedure for preparation of N,N-bis(dialkanol) amides: 1.0 equivalent of fatty methyl ester was heated to 150° C. with 0.9 equivalent of dialkanol amine for approximately 4 hours at 1 atmosphere, and then held at 100° C. for 1 hour at 400 mm Hg. This procedure generally gives a mixture of N,N-bis(dialkanol) fatty amide to amino ester ratio as described in the proceeding tables with a dialkanol amine content of about 5%.

Example 2

Heat 1.0 equivalent of methyl cocoate to 150° C. with 0.9 equivalent of diethanol amine according to the procedure of Example 1.

Example 3

Heat 1.0 equivalent of methyl oleate to 150° C. with 0.9 equivalent of diethanol amine according to the procedure of Example 1.

Example 4

Heat 1.0 equivalent of methyl stearate to 150° C. with 0.9 equivalent of diethanol amine according to the procedure of Example 1.

Example 5

Example 4 was made from the triglyceride of cocoate. In order to reach a DEA: Ester CMR of 0.9, extra DEA was added to further react with the triglyceride.

Example 6

Example 6 shows the aging of Example 2 at 70° C., 80° C., 90° C., 100° C., and 110° C. and the effect these various temperatures have on the amide/ester ratio at various time intervals (FIG. 1).

Example 7

Figure 2:
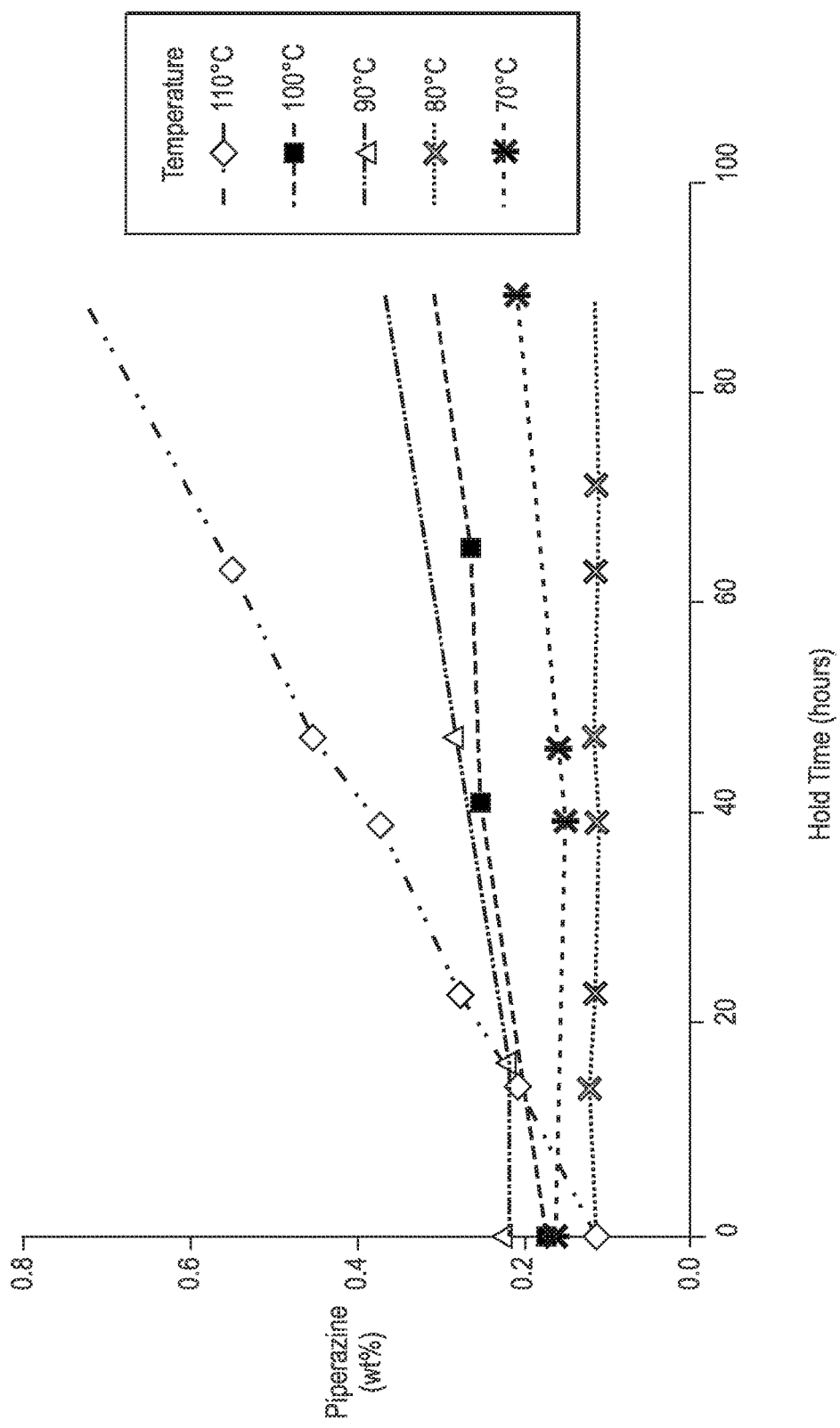
FIG. 2 shows the aging of Example 2 at 70° C., 80° C., 90° C., 100° C., and 110° C. and the effect these various temperatures have on the piperazine (BHEP) content at various time intervals.

Example 7 shows the aging of Example 2 at 70° C., 80° C., 90° C., 100° C., and 110° C. and the effect these various temperatures have on the piperazine (BHEP) content ratio at various time intervals (FIG. 2).

Example 8

Example 2 Neat 80° C. Aging Summary: Example 2 neat normally takes 3-5 months at ambient temperature to reach a DEA content around 1% and amide/ester ratio of greater than 4 after production. Holding the product at 80° C. reduces this aging period to 3-4 days without degradation.

Example 2 starting from methyl cocoate serves as a baseline for 80° C. aging process. Within a timeframe of 100 hours, A/E ratio increased and reached a plateau at around 3.5; % DEA decreased and reached a valley around 1.5% (Table 2). The resulting product after 80° C. aging was comparable to that after 3-5 months' room temperature aging.

TABLE 2

Example 8 Aged at 80° C. for Approximately 4 Days

| Example 8 (Methyl Cocoate + DEA) | | | % Increase in | % Reduction in |
|---|---|---|---|---|
| Hours | A/E Ratio | % DEA | A/E Ratio | DEA |
| 0.00 | 2.25:1 | 4.7 | 0 | 0 |
| 23.00 | 2.66:1 | 3.60 | 18.2 | 23.4 |

TABLE 2-continued

Example 8 Aged at 80° C. for Approximately 4 Days

| Example 8 (Methyl Cocoate + DEA) | | | % Increase in | % Reduction in |
|---|---|---|---|---|
| Hours | A/E Ratio | % DEA | A/E Ratio | DEA |
| 47.00 | 3.03:1 | 2.46 | 34.7 | 47.7 |
| 71.00 | 3.22:1 | 1.97 | 43.1 | 58.1 |
| 95.00 | 3.36:1 | 1.67 | 49.3 | 64.5 |
| 112.00 | 3.40:1 | 1.7 | 51.1 | 63.8 |

Comparative Example 1

Comparative Example 1 shows the aging of example 2 at room temperature for 149 days. Compare this to Example 8 which takes only about 4 days to reach similar values for % DEA and A/E ratio (Table 3).

TABLE 3

Example 2 Aged at Room Temperature for 149 Days (~5 months)

| Elapsed Days | % DEA | A/E ratio |
|---|---|---|
| 0 | | 1.90:1 |
| 22 | | 2.60:1 |
| 93 | | 3.40:1 |
| 67 | 5.2 | |
| 105 | 2.6 | |
| 109 | 2.5 | |
| 130 | 1.2 | 4.10:1 |
| 133 | 1.2 | |
| 134 | | 4.10:1 |
| 149 | 1.4 | |

Example 9

Example 9 shows the aging of Example 5 at 80° C. The mixture was held at 80° C. and underwent a similar process as in Example 8 neat aging. The A/E ratio and % DEA profile also resembled that of Example 8.

The final product after 80° C. aging had an A/E ratio of 5 and % DEA of around 2.35%. A similar sample (Example 8) started with triglyceride (DEA:Ester CMR=0.9) was aged at ambient temperature for 5 months after production and had an A/E Ratio of 5 and % DEA of 1%. The data surprisingly show that 80° C. is effective in accelerating reaction between extra DEA added and excess triglyceride in Example 9, without degrading the active ingredient (Table 4).

TABLE 4

Example 9 Aged at 80° C. for Approximately 4 Days

| Example 9 (Triglyceride + DEA) | | | % Increase in | % Reduction |
|---|---|---|---|---|
| Hours | A/E Ratio | % DEA | A/E Ratio | in DEA |
| 0.00 | 2.84:1 | 7.07 | 0 | 0 |
| 15.25 | 3.59:1 | 4.92 | 26.4 | 30.4 |
| 38.75 | 4.47:1 | 3.29 | 57.4 | 53.5 |
| 64.00 | 4.87:1 | 2.51 | 71.4 | 64.5 |
| 86.75 | 5.00:1 | 2.32 | 76.1 | 67.2 |
| 89.75 | 5.00:1 | 2.35 | 76.1 | 67.2 |

Example 10

Example 10 shows the aging of Example 3 at 80° C. Example 10 is made from methyl oleate. Example 10 was also aged at 80° C., reflected in increased A/E ratio and decreased % DEA. The aging profile of Example 10 (Table 5) was similar to that of Example 8. Example 10 with and without 80° C. aging both continued to ripen at ambient temperature during a 3-month storage period.

TABLE 5

Example 10 Aged at 80° C. for Approximately 3 Days

| Example 10 (Methyl Oleate + DEA) | | | % Increase in | % Reduction |
|---|---|---|---|---|
| Hours | A/E Ratio | % DEA | A/E Ratio | in DEA |
| 0.00 | 1.55:1 | 6.25 | 0 | 0 |
| 16.25 | 1.99:1 | 4.60 | 28.4 | 26.4 |
| 39.25 | 2.51:1 | 3.24 | 61.9 | 48.2 |
| 63.25 | 2.81:1 | 2.56 | 81.3 | 59.0 |
| 71.25 | 2.88:1 | 2.19 | 85.8 | 65.0 |
| 71.25 | 2.89:1 | 2.14 | 85.8 | 65.8 |

Example 11

Example 11 shows the aging of Example 4 at 80° C. Example 11 is made from methyl stearate. The 80° C. aging profile for Example 11 was similar to that of Example 8 and 10, except that the A/E ratio was relatively low both at the beginning and at the end of 80° C. aging. Although % DEA decreased to around 1% after 5 months room temperature aging, the A/E ratio didn't reach 3 for samples either with or without 80° C. aging (Table 6).

TABLE 6

Example 11 Aged at 80° C. for Approximately 4 Days

| Example 11 (Methyl Stearate + DEA) | | | % Increase in | % Reduction |
|---|---|---|---|---|
| Hours | A/E Ratio | % DEA | A/E Ratio | in DEA |
| 0.00 | 1.26:1 | 6.39 | 0 | 0 |
| 23.33 | 1.92:1 | 3.77 | 52.4 | 41.0 |
| 47.83 | 2.36:1 | 2.67 | 87.3 | 58.2 |
| 71.75 | 2.61:1 | 2.60 | 107.1 | 59.3 |
| 95.50 | 2.89:1 | 1.96 | 129.4 | 69.3 |

Example 12

Example 12 shows a comparison of the aging profiles of examples 8, 10, and 11 (Table 7).

TABLE 7

| | Example 8 | | Example 10 | | Example 11 | |
|---|---|---|---|---|---|---|
| | A/E Ratio | % DEA | A/E Ratio | % DEA | A/E Ratio | % DEA |
| After Production | 2.25:1 | 4.70 | 1.50:1 | 7.40 | 1.36:1 | 6.60 |
| R.T. Aged[a] | 3.82:1 | 1.51 | 2.74:1 | 2.72 | 2.65:1 | 1.39 |

TABLE 7-continued

| | Example 8 | | Example 10 | | Example 11 | |
|---|---|---|---|---|---|---|
| | A/E Ratio | % DEA | A/E Ratio | % DEA | A/E Ratio | % DEA |
| 80° C. Aged[b] | 3.40:1 | 1.67 | 2.86:1 | 3.00 | 2.76:1 | 1.70 |
| 80° C. Aged, R.T. further Aged[a] | 4.06:1 | 0.66 | 3.61:1 | 1.29 | 2.59:1 | 0.50 |

[a]5 months for Example 8 and Example 10, 3 months for Example 11.
[b]approximately 4 days.

Comparative Example 2

The ineffectiveness of high temperature reaction in terms of driving the equilibrium towards more amide is demonstrated by the example below.

1.0 equivalent, 190 grams of coco methyl ester was heated at 150° C. with 0.9 equivalent, 78.96 grams of diethanol amine, the IR ratio of amide band and ester band was stabilized at 2.6 with prolonged heating. The IR ratio somewhat leveled out and even dropped (Table 8).

TABLE 8

| Time | 0 Min | 30 Min | 60 Min | 90 Min | 120 Min | 150 Min | 180 Min | 195 Min | 240 Min | 285 Min | 300 Min |
|---|---|---|---|---|---|---|---|---|---|---|---|
| Amide/ester ratio | 0.000 | 0.315 | 0.206 | 0.954 | 1.493 | 1.933 | 2.345 | 2.627 | 2.918 | 2.947 | 2.600 |

The aging process can be greatly improved by using temperatures that are higher than the room temperature and lower than the reaction high temperature. At these temperatures, there is just enough energy to overcome the energy barrier from ester to amide but not enough energy to overcome the energy barrier from amide to ester. The temperature ranges of 70 to 90° C. allow the equilibrium to move only one way—from ester to amide at a much faster kinetics as compared to the aging process at room temperature.

Example 13

Reaction of cocomethyl ester and diisopropanol amine: 1.0 equivalent, 10 gram of methyl cocoate was reacted with 0.9 equivalent, 5.26 gram of diethanol amine at 150° C. for 5 hours. Aging results were compared between room temperatures and at 80° C. (Table 9).

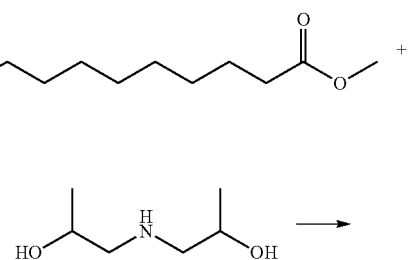

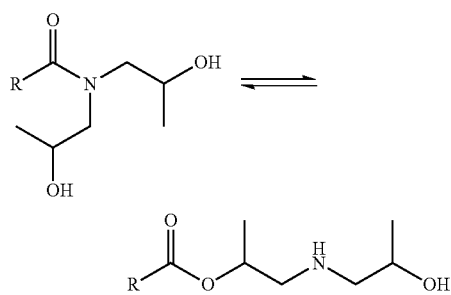

TABLE 9

| Time (hours) | A/E Ratio (Aging at 80° C.) | A/E Ratio (Aging at Room Temp.) |
|---|---|---|
| 2 | 0.36:1 | |
| 18 | 0.48:1 | |
| 24 | | 0.27:1 |
| 25 | 0.51:1 | |
| 66 | 0.67:1 | |
| 72 | | 0.31:1 |
| 73 | 0.71:1 | |
| 82 | 0.77:1 | |
| 96 | | 0.32:1 |
| 106 | 0.91:1 | |
| 130 | 1.07:1 | |

Example 14

Reaction of cocomethyl ester with ethanol amine: 1.0 equivalent, 15 grams cocomethyl ester was reacted with 0.9 equivalent, 3.6 grams of ethanol amine at 120° C. for 5 hour with a product of A/E ratio 2.11 (Table 10).

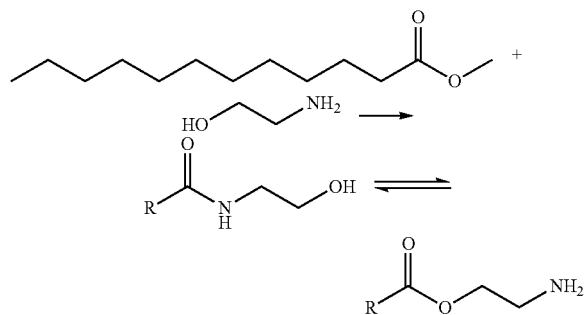

TABLE 10

| | aging under 80 C. | | | | |
|---|---|---|---|---|---|
| time | 18 hr | 25 hr | 42 hr | 49 hr | 73 hr |
| A/E ratio | 6.83 | 10.8 | 7.11 | 9.18 | 10.8 |
| | aging under R.T | | | | |
| time | 1 day | | 2 day | | 3 day |
| A/E ratio | 2.52 | | 3.18 | | 4.11 |

| Time (hours) | A/E Ratio (Aging at 80° C.) | % Increase in A/E Ratio | A/E Ratio (Aging at Room Temp.) | % Increase in A/E Ratio |
|---|---|---|---|---|
| 0 | 2.11:1 | | 2.11:1 | |
| 18 | 6.83:1 | 223.7 | | |
| 24 | | | 2.52:1 | 4.27 |
| 25 | 10.8:1 | 411.8 | | |
| 42 | 7.11:1 | 237 | | |
| 48 | | | 3.18:1 | 50.7 |
| 49 | 9.18:1 | 335.1 | | |
| 72 | | | 4.11:1 | 94.8 |
| 73 | 10.8:1 | 411.8 | | |

As demonstrated by the working examples presented herein, it is evident that samples aged at 80° C. for 3-4 days comprise higher amide/ester ratios and lower levels of dialkanolamine than their analogous samples aged at room temperature.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A method for aging a composition comprising the steps of:
   a) providing a mixture comprising:
      i. an amide reaction product of an about $C_{12}$ to about $C_{22}$ fatty alkyl ester and a mono-alkanolamine or a dialkanolamine wherein the alkyl group of the mono-alkanolamine or the dialkanolamine has from 2 to 4 carbon atoms,
      ii. an ester reaction product of the about $C_{12}$ to about $C_{22}$ fatty alkyl ester and the mono-alkanolamine or the dialkanolamine, and
   b) maintaining the mixture from (a) at a temperature from 70° C. to 90° C. for a period of time sufficient to increase the ratio of the amide reaction product to the ester reaction product by at least 15%, wherein the time sufficient to increase the ratio of the amide reaction product to the ester reaction product by at least 15% is an aging time of from 15.25 to 112 hours.

2. The method of claim 1, wherein the mixture further comprises an unreacted mono-alkanolamine or an unreacted dialkanolamine and an unreacted about $C_{12}$ to about $C_{22}$ fatty alkyl ester.

3. The method of claim 1, wherein the monoalkanolmine is ethanolamine.

4. The method of claim 1, wherein the dialkanolamine is diethanolamine or diisopropanolamine.

5. The method of claim 1, wherein the amide reaction product is selected from the group consisting of N,N-bis(2-hydroxyethyl)dodecanamide, N,N-bis(2-hydroxyethyl)oleamide, N,N-bis(2-hydroxyethyl)stearamide, N,N-bis(2-hydroxypropyl)dodecanamide, and N-(2-hydroxyethyl)dodecanamide.

6. The method of claim 1, wherein the ratio of the dialkanol fatty amide to the alkyl ester in the mixture is increased by at least 20%.

7. The method of claim 1, wherein the fatty alkyl ester is a methyl ester or ethyl ester.

8. The method of claim 1, wherein the temperature in step b) is from 70 to 85° C.

9. The method of claim 1, wherein the temperature in step b) is from 75 to 85° C.

10. The method of claim 1, wherein the temperature in step b) is from 75 to 80° C.

11. The method of claim 1, wherein the temperature in step b) is about 80° C.

12. The method of claim 1, wherein the alkanolamide to ester ratio of the aged product is at least 0.1:1.0.

13. The method of claim 1, wherein the alkanolamide to ester ratio of the aged product is at least 0.1:1.0 to 12:1.

14. The method of claim 1, wherein the alkanolamide to ester ratio of the aged product is at least 0.2:1.0 to 6:1.

15. The method of claim 1, and further wherein the reduction in the alkanolamine of the aged product is from 20 to 70%.

16. The method of claim 1, wherein the reduction in alkanolamine of the aged product is from 25 to 60%.

17. The method of claim 1, wherein the reduction in alkanolamine of the aged product is from 25 to 50%.

18. The method of claim 1, wherein the reduction in alkanolamine of the aged product is from 25 to 40%.

19. The method of claim 1, wherein the reduction in alkanolamine of the aged product is from 25 to 30%.

20. The method of claim 1, wherein the aging time is from 10 to 96 hours.

21. The method of claim 1, wherein the aging time is from 30 to 96 hours.

22. The method of claim 1, wherein the aging time is from 50 to 96 hours.

23. The method of claim 1, wherein the aging time is from 70 to 96 hours.

24. The method of claim 1, wherein the aging time is from 80 to 96 hours.

25. The method of claim 1, wherein the aging time is 96 hours.

26. A method for aging a composition comprising the steps of:
   a) providing a reaction mixture comprising an about $C_{12}$ to about $C_{22}$ fatty acid alkyl ester, a mono-alkanolamine or a dialkanolamine wherein the alkyl group of the mono-alkanolamine or the dialkanolamine has from 2 to 4 carbon atoms and a reaction product of an about $C_{12}$ to about $C_{22}$ fatty acid alkyl ester and a mono-alkanolamine or a dialkanolamine wherein the alkyl group of the mono-alkanolamine or the dialkanolamine has from 2 to 4 carbon atoms, wherein the reaction product comprises:
      i. an amide reaction product, and
      ii. an ester reaction product,
      and
   b) maintaining the mixture from (a) at a temperature from 70° C. to 90° C. for a period of time sufficient to increase the ratio of the amide reaction product to the ester reaction product by at least 15%, wherein the time sufficient to increase the ratio of the amide reaction product to the ester reaction product by at least 15% is an aging time of aging time is from 15.25 to 112 hours.

27. A method comprising the steps of:
   (a) reacting an about $C_{12}$ to about $C_{22}$ fatty alkyl ester with a mono-alkanolamine or a dialkanolamine wherein the alkyl group of the mono-alkanolamine or the dialkanolamine has from 2 to 4 carbon atoms to form a mixture comprising (i) an amide reaction product, and (ii) an ester reaction product, and
   (b) maintaining the mixture from step (a) at a temperature from 70° C. to 90° C. for a period of time sufficient to increase the ratio of the amide reaction product to the ester reaction product by at least 15%, wherein the time sufficient to increase the ratio of the amide reaction product to the ester reaction product by at least 15% is an aging time of from 15.25 to 112 hours.

* * * * *